(12) United States Patent
Hsiao et al.

(10) Patent No.: US 8,212,002 B2
(45) Date of Patent: Jul. 3, 2012

(54) SYNTHESIS OF GLATIRAMER ACETATE

(75) Inventors: Tsung-Yu Hsiao, Kaohsiung County (TW); Meng-Fen Ho, Anding Township, Tainan County (TW)

(73) Assignee: Scinopharm Taiwan Ltd, Tainan (TW)

( * ) Notice: Subject to any disclaimer, the term of this patent is extended or adjusted under 35 U.S.C. 154(b) by 309 days.

(21) Appl. No.: 12/536,023

(22) Filed: Aug. 5, 2009

(65) Prior Publication Data

US 2010/0036092 A1 Feb. 11, 2010

Related U.S. Application Data

(60) Provisional application No. 61/188,216, filed on Aug. 7, 2008.

(51) Int. Cl.
| | |
|---|---|
| *A61K 38/00* | (2006.01) |
| *C07K 1/00* | (2006.01) |
| *C07K 2/00* | (2006.01) |
| *C07K 4/00* | (2006.01) |
| *C07K 7/00* | (2006.01) |
| *C07K 14/00* | (2006.01) |
| *C07K 16/00* | (2006.01) |
| *C07K 17/00* | (2006.01) |

(52) U.S. Cl. .................. 530/337; 530/300
(58) Field of Classification Search .............. None
See application file for complete search history.

(56) References Cited

U.S. PATENT DOCUMENTS

| | | |
|---|---|---|
| 3,849,550 A | 11/1974 | Teitelbaum et al. |
| 5,800,808 A | 9/1998 | Konfino et al. |
| 2002/0147302 A1 | 10/2002 | Abdel-Magid et al. |
| 2006/0052586 A1* | 3/2006 | Dolitzky .............. 530/402 |
| 2006/0154862 A1 | 7/2006 | Ray et al. |
| 2006/0172942 A1 | 8/2006 | Dolitzky |
| 2007/0141663 A1 | 6/2007 | Din et al. |
| 2009/0035816 A1 | 2/2009 | Chan et al. |

OTHER PUBLICATIONS

Ruggieri et al. Glatiramer Acetate in Multiple Sclerosis: A Review. CNS Drug Reviews, Jun. 2007. vol. 13, No1. 2, pp. 178-191.*
International Search Report dated Sep. 24, 2009.

* cited by examiner

*Primary Examiner* — Marcela M Cordero Garcia
(74) *Attorney, Agent, or Firm* — VLP Law Group LLP

(57) ABSTRACT

A process of making a polylpeptide or a pharmaceutically acceptable salt thereof comprises reacting a L-lysine protected polypeptide, which comprises L-alanine, L-tyrosine, L-glutamate, and L-lysine that is protected with a protecting group, with a tetraalkylammonium hydroxide in water to remove the protecting group.

20 Claims, No Drawings

SYNTHESIS OF GLATIRAMER ACETATE

RELATED APPLICATIONS

This application claims priority from U.S. Provisional Patent Application Ser. No. 61/188,216 which was filed on Aug. 7, 2008. The entire content of this provisional application is incorporated herein as reference.

BACKGROUND OF THE INVENTION

1. Field of the Invention

The present application relates to a process for the synthesis of polypeptides comprising the following amino acid units in the structure, namely, L-alanine, L-glutamic acid, L-lysine, and L-tyrosine. Glatiramer acetate, also known as copolymer-1, is a representative polypeptide of the present invention 2. Description of the Related Art Glatiramer acetate is a mixture of polypeptides which has been approved for the treatment of multiple sclerosis. It is a mixture of acetate salts of chemically synthetic polypeptides, containing four naturally occurring amino acids: L-alanine, L-glutamic acid, L-lysine, and L-tyrosine typically with an average molar ratio of 0.392-0.462, 0.129-0.159, 0.300-0.374, and 0.086-01000, respectively. The average molecular weight of glatiramer acetate is 4,700-11,000 daltons.

Chemically, glatiramer acetate is designated L-glutamic acid polymer with L-alanine, L-lysine and L-tyrosine, acetate (salt). Its structural formula is: (Glu, Ala, Lys, Tyr)$_x$·xCH$_3$COOH. Its CAS number is 147245-9-2-9.

Processes for preparing polypeptides of this type, including glatiramer acetate, have been described in U.S. Pat. Nos. 3,849,550 and 5,800,808; U.S. Patent Publication Nos. 2006/0172942; 2006/0154862; and 2007/0141663. The entire content of these patents and patent publications is incorporated herein as reference. The process for the preparation of the polypeptides of this type is based on the copolymerization of N-carboxyanhydride of tyrosine, N-carboxyanhydride of L-alanine, N-carboxyanhydride of protected L-glutamic acid and N-carboxyanhydride of protected L-lysine to form a protected copolymer. The deblocking of the protected L-glutamic acid is effected by acidolysis or hydrogenolysis (first deprotection) and is followed by the removal of the protecting group from L-lysine by base cleavage (second deprotection).

Typically, L-lysine is protected by a trifluoroacetyl group, and a nitrogen base with weak basicity, such as piperidine, is used to remove the protecting group of the L-Lysine. The nitrogen base usually has a concentration of more than 1 M in an amount of more than 35 molar equivalents of the L-lysine. Such a method is neither economic nor environmental.

Therefore, improvement of production of a polypeptide, such as glatiramer acetate, is desirable.

SUMMARY OF THE INVENTION

The present application provides a process of making a polylpeptide or a pharmaceutically acceptable salt thereof. The polylpeptide comprises L-alanine, L-tyrosine, L-glutamate, and L-lysine. The process comprises reacting a L-lysine protected polypeptide, which comprises L-alanine, L-tyrosine, L-glutamate, and L-lysine that is protected with a first protecting group, with a tetraalkylammonium hydroxide in water to remove the first protecting group.

Preferably, the tetra alkylammonium hydroxide is tetra $C_1$-$C_8$ alkylammonium hydroxide. More preferably, the tretraalkylammonium hydroxide is tetramethylammonium hydroxide, tetraethylammonium hydroxide, or tetrabutylammonium hydroxide, in particular tetrabutylammonium hydroxide.

The first protecting group may be any group that can protect lysine from undesired reaction and can be easily removed subsequently. For example, the lysine may be protected as carbomate and/or amide by an alkoxy or aroxy carbonyl group and/or an alkyl or aryl carbonyl group, more preferably, by a group selected from methoxycarbonyl, ethoxycarbonyl, 9-fluorenylmethyloxycarbonyl, trifluoroacetyl, 2,2,2-trichloroethoxycarbonyl, trichioroacetyl, picolinyl and combinations thereof. More particularly, the first protecting group is trifluoroacetyl.

The L-lysine protected polypeptide may be prepared by any suitable method. Preferably, it may be prepared by a process comprising;

a) polymerizing a mixture of the N-carboxyanhydrides of L-alanine, L-tyrosine, L-glutamate that is protected with a second protecting group, and L-lysine that is protected with the first protecting group in a solvent to obtain a protected polypeptide; and b) removing the second protecting group to obtain the L-lysine protected polypeptide.

Alternatively, at least one of the amino acids used in the polymerizing step can be in a form of N-thiocarboxyanhydride, rather than N-carboxyanhyride (see U.S. Patent Application Publication No. 2009/0035816, the entire content of which is herein incorporated as reference).

The second protecting group may be any suitable group that can protect L-glutamate from undesired reaction and can be easily removed subsequently. For example, the L-glutamate may be protected as ester by an alkyl group and/or an aromatic group, preferably by a group selected from cyclohexyl, benzyl, t-butyl, allyl ester, adamantyl, 9-fluorenylmethyl, and combinations thereof. More preferably, the second protecting group is selected from the group consisting of benzyl and t-butyl, in particular benzyl.

Removal of the second protecting group step (i.e., deprotecting) may be accomplished by, for example, base cleavage, acidolysis, thiolysis, hydrogenation, or enzyme-catalyzed hydrolysis.

In accordance with one embodiment of the present invention, the deprotecting step comprises adding an acid to the protected polypeptide. The acid can be, for example, hydrobromide, trifluoroacetic acid, or hydrogen chloride in a solvent medium selected from acetic acid, dioxane, ethyl acetate, and mixtures thereof. As a preferred embodiment, the acid is hydrobromic acid dissolved in acetic acid. Preferably, the process comprises a further step of washing the reaction mixture formed during the deprotecting step with a $C_5$-$C_{12}$ alkane, in particular heptane.

The polylpeptide or a pharmaceutically acceptable salt thereof made in accordance with the process of the present application is preferably glatiramer acetate.

The concentration of the tetraalkylammonium hydroxide base is preferably about 0.5 M. The amount of the tetraalkylammonium hydroxide base is less than 10, preferably from 1.5 to 6, more preferably about 3 molar equivalents relative to the molar amount of L-lysine that is protected with the first protecting group.

Preferably, after the first protecting group is removed and the polypeptide is synthesized, the process comprises a step of purifying and isolating the polypeptide by dialysis. More preferably, this purifying and isolating is carried out before any other purifying and isolating step, if any. The polypeptide may be isolated or purified by a single dialysis against water.

As a preferred embodiment, the tetraalkylammonium hydroxide base used in the present invention may have a concentration of about 40% (by weight) in water. The molar amount of treralkylammonium hydroxide base relative to the lysine protected with the first protecting group may be 1.5-6. The amount of the water used during the removing of the first protecting group may be about 10 parts by weight relative to the amount of lysine protected polypeptide. Other conditions of the reaction of removing the first protecting group may include: reaction temperature: 20~25° C., reaction time: 24 hours, and reaction pressure: normal atmosphere pressure.

In accordance yet with another embodiment, the present application provides a new polypeptide produced in accordance with the process described above.

Compared to other methods, the process of the present application has the following advantages:

Applicants found an oxygen base with slightly stronger basicity than a nitrogen base with weak basicity, such as piperidine, to de-protect the first protecting group. To accomplish the removal of the first protecting group, the molar amount of the base used in the present application relative to the lysine protected with the first protecting group can be much less than that of the nitrogen base used in methods described by other publications. The concentration of the oxygen base used in the present application may also be much less than that of the nitrogen base used by other methods. The concentration of the polypeptide polymer obtained in above reaction is higher than that obtained by other methods known to Applicants. Therefore, the process in accordance with the present invention is much more economic and renders the workup easier than other reported methods. In addition, because the dialysis can be conducted after workup instead of workup after dialysis as described by other publications, the process of the present application can save workup time for the product preparation.

The various features of novelty which characterize the invention are pointed out with particularity in the claims annexed to and forming a part of the disclosure. For a better understanding of the invention, its operating advantages, and specific objects attained by its use, reference should be had to the descriptive matter in which there are illustrated and described preferred embodiments of the invention.

DETAILED DESCRIPTION OF THE PRESENTLY PREFERRED EMBODIMENTS

The following examples are provided to illustrate, but not to limit, embodiments in accordance with the present invention. In accordance with an embodiment of the present invention, and as illustrated by examples below, the process of making copolymer involves preparing a protected copolymer from the polymerization of N-carboxyanhydride of L-alanine, N-carboxyanhydride of γ-benzyl L-glutamate, N-carboxyanhydride of N-trifluoroacetyllysine, and N-carboxyanhydride of L-tyrosine. The protection groups are removed by 33% HBr/HOAc followed by tetraalkylammonium hydroxide in water to obtain glatiramer.

Glatiramer acetate may be obtained by purification of the copolymer through dialysis, followed by treatment with acetic acid to form the acetate salt. As an embodiment, the process therefor may involve the polymerization of four N-carboxyanhydride, two purification steps and one acetate salt formation step.

EXAMPLE 1

Preparation of Protected Copolymer

N-carboxyanhydride of L-alanine (4.0 g, 34.78 mmol), N-carboxyanhydride of γ-benzyl L-glutamate (3.0 g, 11.39 mmol), N-carboxyanhydride of N-trifluoroacetyllysine (7.47 g, mol), and N-carboxyanhydride of L-tyrosine (1.6 g, 7.73 mmol) were placed in a single-neck flask with a magnetic stirrer. To this mixture was dissolved by adding dry dioxane (289 mL). Distilled diethylamine (60 μL) was added. The resulting mixture was stirred mechanically for 24 hours at room temperature. Acetone (116 mL) was added to the mixture and the solution was slowly poured into a mixture of acetone (173 mL) and water (578 mL). The suspension was stirred and filtered. The solid was dried under vacuum at NMT 45° C. to give 12.02 g of protected copolymer (94.7% of yield).

EXAMPLE 2

Removing benzyl protection group from poly[L-Ala, 5-benzyl-L-Glu, N6-TFA-L-Lys, L-Tyr] to form poly[L-Ala, L-Glu, N6-TFA-L-Lys, L-Tyr]

12.02 g of protected copolymer, synthesized as described in Example 1, was suspended in 72 mL of 33% HBr/HOAc. The mixture was stirred at room temperature for 17 hours and the solution became clear. The mixture was extracted and washed with n-heptane (190 mL). The lower layer of the mixture was transferred into a mixture of water (240 mL) and n-heptane(120 mL). The precipitate was filtrated and dried to give trifluoroacetyl-glatiramer as a white solid.

EXAMPLE 3

Removing trifluoroacetyl protection group from poly[L-Ala, L-Glu, N6-TFA-L-Lys, L-Tyr] to form poly[L-Ala, L-Glu, L-Lys, L-Tyr]

9.5 g of trifluoroacetyl-glatiramer, synthesized in Example 2 was reacted with water (120.2 mL) and 40% tetrabutylammonium hydroxide in water (52.2 mL, 3 eq) for 24 hours at room temperature. The mixture was adjusted its pH to 3~4 by acetic acid (20 mL) to give a glatiramer acetate solution. Ultrafiltration was performed using a 3 kilodalton membrane to remove the low-molecular weight impurities. After 2 cycles of continuous water ultrafiltration, the resulting solution is concentrated and lyophilized to give glatiramer acetate as a pure white solid (4.7 g, 60% yield).

EXAMPLE 4

Removing trifluoroacetyl protection group from poly[L-Ala, L-Glu, N6-TFA-L-Lys, L-Tyr] to form poly[L-Ala, L-Glu, L-Lys, L-Tyr]

0.12 g of trifluoroacetyl-glatiramer, synthesized in Example 2 was reacted with water (1.2 mL) and 25% tetramethylammonium hydroxide in water (0.32 mL, 3 eq) for 24 hours at room temperature. The mixture was adjusted its pH to 3~4 by acetic acid (0.2 mL) to give a glatiramer acetate solution. Ultrafiltration was performed using a 3 kilodalton membrane to remove the low-molecular weight impurities. After 2 cycles of continuous water ultrafiltration, the resulting solution is concentrated and lyophilized to give glatiramer acetate as a pure white solid (39 mg, 42% yield).

EXAMPLE 5

Removing trifluoroacetyl protection group from poly[L-Ala, L-Glu, N6-TFA-L-Lys, L-Tyr] to form poly[L-Ala, L-Glu, L-Lys, L-Tyr]

0.20 g of trifluoroacetyl-glatiramer, synthesized in Example 2 was reacted with water (2.0 mL) and 20% tetraethylammonium hydroxide in water (1.02 mL, 3 eq) for 24 hours at room temperature. The mixture was adjusted its pH to 3~4 by acetic acid (0.5 mL) to give a glatiramer acetate solution. Ultrafiltration was performed using a 3 kilodalton membrane to remove the low-molecular weight impurities. After 2 cycles of continuous water ultrafiltration, the resulting solution is concentrated and lyophilized to obtain glatiramer acetate as a pure white solid (76.7 mg, 49% yield).

The invention is not limited by the embodiments described above which are presented as examples only but can be modified in various ways within the scope of protection defined by the appended patent claims.

We claim:

1. A process of making a polylpeptide or a pharmaceutically acceptable salt thereof, wherein the polypeptide comprises L-alanine, L-tyrosine, L-glutamate, and L-lysine, and the process comprises reacting a L-lysine protected polypeptide, which comprises L-alanine, L-tyrosine, L-glutamate, and L-lysine that is protected with a first protecting group, with a tetraalkylammonium hydroxide in water to remove the first protecting group, and wherein the L-lysin protected polypeptide is prepared by a process comprising:
   a) polymerizing a mixture of the N-carboxyanhydrides of L-alanine, L-tyrosine, L-glutamate that is protected with a second protecting group, and L-lysine that is protected with the first protecting group n a solvent to obtain a protected polypeptide; and
   b) reacting the protected polypeptide in step a) with hydrobromic acid in acetic acid to remove the second protecting group and to obtain the L-lysine protected polypeptide.

2. The process of claim 1 wherein the tetraalkylammonium hydroxide is tetra $C_1$-$C_8$ alkylammonium hydroxide.

3. The process of claim 1 wherein the tretraalkylammonium hydroxide is selected from the group consisting of tetramethylammonium hydroxide, tetraethylammonium hydroxide, tetrabutylammonium hydroxide, and combinations thereof.

4. The process of claim 1 wherein the tretraalkyl ammonium is tetrabutylammonium hydroxide.

5. The process of claim 1 wherein the first protecting group is selected from groups of alkylcarbonyl, alkoxycarbonyl, arylcarbonyl, aroxycarbonyl and their substituted derivatives.

6. The process of claim 1 wherein the first protecting group is trifluoroacetyl.

7. The process of claim 1 comprising a further step of washing the reaction mixture formed during the reaction of the protected polypeptide with hydrobromic acid in acetic acid with a $C_5$-$C_{12}$ alkane.

8. The process of claim 1, wherein the $C_5$-$C_{12}$ alkane is heptane.

9. The process of claim 1 wherein the second protecting group is selected from the group consisting of benzyl and t-butyl, 10. The process of claim 1 wherein the second protecting group is benzyl.

11. The process of claim 1 wherein the polylpeptide or a pharmaceutically acceptable salt thereof is glatiramer acetate.

12. The process of claim 1 wherein the amount of the tetraalkylammonium hydroxide base is less than 10 molar equivalents to the L-lysine that is protected with the first protecting group.

13. The process of dam 1 wherein the amount of the tetraalkylammonium hydroxide base is from 1.5 to 6 molar equivalents to the L-lysine that is protected with the first protecting group.

14. The process of claim 1 wherein the amount of the tetraalkylamrnonium hydroxide base is about 3 molar equivalents to the L-lysine that is protected with the first protecting group.

15. The process of claim 1 wherein the process comprises a step of purifying and isolating the polypeptide by dialysis prior to any other step of purifying and isolating the polypeptide.

16. A process of making a polypeptide or a pharmaceutically acceptable salt thereof, wherein the polylpeptide comprises L-alanine, L-tyrosine, L-glutamate, and L-lysine, and the process comprises reacting a L-lysine protected polypeptide, which comprises L-alanine, L-tyrosine, L-glutamate, and L-lysine that is protected as an amide with a first protecting group, with a tetraalkylammonium hydroxide in water to remove the first protecting group.

17. The process of claim 16 wherein the first protecting group is selected from a group consisting of alkylcarbonyl, alkoxycarbonyl, arylcarbonyl, aroxycarbonyl, their substituted derivatives, and combinations thereof.

18. The process of claim 16 wherein the first protecting group is selected from a group consisting of methoxycarbonyl, ethoxycarbonyl, 9-fluorenylmethyloxycarbonyl, trifluoroacetyl, 2,2,2-trichloroethoxycarbonyl, trichloroacetyl, picolinyl, and combinations thereof.

19. The process of claim 16 wherein the first protecting group is trifluoroacetyl.

20. The process of claim 16 wherein the reacting is conducted at room temperature for about 24 hours.

* * * * *

UNITED STATES PATENT AND TRADEMARK OFFICE
CERTIFICATE OF CORRECTION

PATENT NO. : 8,212,002 B2
APPLICATION NO. : 12/536023
DATED : July 3, 2012
INVENTOR(S) : Tsung-Yu Hsiao et al.

Page 1 of 1

It is certified that error appears in the above-identified patent and that said Letters Patent is hereby corrected as shown below:

In the Claims

The word "n" at claim 1, Column 5, line 31 (Approximately) should read --in--

Signed and Sealed this
First Day of March, 2016

Michelle K. Lee
*Director of the United States Patent and Trademark Office*